(12) United States Patent
Maeda et al.

(10) Patent No.: US 8,567,441 B2
(45) Date of Patent: Oct. 29, 2013

(54) SAMPLE INTRODUCTION DEVICE

(75) Inventors: Yoshiaki Maeda, Kyoto (JP); Shuzo Maruyama, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 419 days.

(21) Appl. No.: 12/667,679

(22) PCT Filed: Sep. 24, 2008

(86) PCT No.: PCT/JP2008/067199
§ 371 (c)(1),
(2), (4) Date: Jan. 4, 2010

(87) PCT Pub. No.: WO2009/041442
PCT Pub. Date: Apr. 2, 2009

(65) Prior Publication Data
US 2010/0206411 A1 Aug. 19, 2010

(30) Foreign Application Priority Data
Sep. 28, 2007 (JP) ................................ 2007-256175

(51) Int. Cl.
*F16K 11/074* (2006.01)
*F16K 3/36* (2006.01)
*F16K 5/22* (2006.01)
*F16K 11/00* (2006.01)
*F16K 51/00* (2006.01)
*G01N 13/00* (2006.01)
*G01N 30/84* (2006.01)

(52) U.S. Cl.
USPC ...................... 137/625.46; 137/240; 73/61.55

(58) Field of Classification Search
USPC .................. 137/597, 625.17, 625.46, 625.47, 137/625.29, 240; 73/61.55, 61.56
See application file for complete search history.

(56) References Cited

U.S. PATENT DOCUMENTS 2,613,056 A * 10/1952 Hughes ..................... 137/625.29
2,631,811 A *  3/1953 Malloy ..................... 137/625.29

(Continued)

FOREIGN PATENT DOCUMENTS

CN   101063495   10/2007
JP   H03-19962    2/1991

(Continued)

OTHER PUBLICATIONS

Shimadzu, "Analytical and Measuring Instruments—Regarding Auto-sampler injection method" Webstie: http://www.an.shimadzu.co.jp/hplc/support/lib/lctalk/46/46tec.htm.

(Continued)

*Primary Examiner* — John K Fristoe, Jr.
*Assistant Examiner* — Frederick D Soski
(74) *Attorney, Agent, or Firm* — J.C. Patents

(57) ABSTRACT

A sample introduction device for reducing carry-over is provided. In the sample introduction device, when a high pressure valve 51 is switched from a load status to an injection status in a total volume injection method, the communication between a stator hole d in communication with an injection port 25 and a stator hole c connected to a flow path toward a separation/detection section 30 occurs earlier than the communication between a stator hole b in communication with a liquid feeder 10 and a stator hole a in communication with a needle 54. A length of a rotor groove Y communicating stator holes d and e or stator holes d and c is set longer than a length of another rotor groove X.

3 Claims, 9 Drawing Sheets

(56) References Cited

U.S. PATENT DOCUMENTS

| | | | |
|---|---|---|---|
| 2,757,541 A * | 8/1956 | Watson et al. | 73/863.73 |
| 4,095,472 A * | 6/1978 | Mowery, Jr. | 73/61.56 |
| 4,102,179 A * | 7/1978 | Snell | 73/61.56 |
| 4,112,743 A * | 9/1978 | Mowery, Jr. | 73/61.56 |
| 4,702,889 A * | 10/1987 | Cabrera et al. | 422/540 |
| 5,010,921 A * | 4/1991 | Nohl | 137/625.46 |
| 5,952,557 A * | 9/1999 | Ikeda et al. | 73/23.42 |
| 6,129,840 A * | 10/2000 | Kitaoka | 210/198.2 |
| 6,498,040 B1 * | 12/2002 | Yokoyama et al. | 436/161 |
| 6,668,623 B2 * | 12/2003 | Tani et al. | 73/61.52 |
| 6,988,511 B2 * | 1/2006 | Tang | 137/625.29 |
| 7,216,528 B2 * | 5/2007 | Gamache et al. | 73/23.41 |
| 7,503,203 B2 * | 3/2009 | Gamache et al. | 73/23.42 |
| 7,526,947 B2 * | 5/2009 | Tatsumi et al. | 73/61.55 |
| 7,566,396 B2 * | 7/2009 | Iwata | 210/198.2 |
| 7,574,901 B2 * | 8/2009 | Iwata | 73/61.56 |
| 7,588,725 B2 * | 9/2009 | Ozbal et al. | 422/63 |
| 2005/0241703 A1 * | 11/2005 | Takacs | 137/625.46 |
| 2007/0144594 A1 * | 6/2007 | Moon et al. | 137/625.46 |
| 2007/0251302 A1 * | 11/2007 | Iwata | 73/61.56 |
| 2008/0229809 A1 * | 9/2008 | Hirayama et al. | 73/61.55 |
| 2008/0229810 A1 * | 9/2008 | Swart et al. | 73/61.55 |
| 2009/0050212 A1 * | 2/2009 | Dourdeville et al. | 137/14 |
| 2009/0078031 A1 * | 3/2009 | Ono et al. | 73/61.55 |
| 2009/0139310 A1 * | 6/2009 | Santiago et al. | 73/61.55 |
| 2009/0145205 A1 * | 6/2009 | Hochgraeber et al. | 73/61.55 |
| 2010/0037919 A1 * | 2/2010 | Doebelin et al. | 137/625.46 |
| 2010/0058841 A1 * | 3/2010 | Wilen | 73/61.56 |
| 2010/0107742 A1 * | 5/2010 | Liu et al. | 73/61.56 |
| 2010/0206411 A1 * | 8/2010 | Maeda et al. | 137/625.17 |
| 2010/0288025 A1 * | 11/2010 | Hochgraeber | 73/61.55 |
| 2011/0209532 A1 * | 9/2011 | Maeda | 73/61.56 |
| 2011/0247403 A1 * | 10/2011 | Liu | 73/61.55 |
| 2011/0247405 A1 * | 10/2011 | Yasunaga et al. | 73/61.55 |

FOREIGN PATENT DOCUMENTS

| | | |
|---|---|---|
| JP | 06-148157 | 5/1994 |
| JP | 10170488 A * | 12/1996 |
| JP | 10-170488 | 6/1998 |
| JP | 2001-255315 | 9/2001 |
| JP | 2001255315 A * | 9/2001 |
| JP | 2004-085499 | 3/2004 |
| JP | 2004085499 A * | 3/2004 |
| JP | 2004-215118 | 7/2004 |
| JP | 2006-038809 | 2/2006 |
| JP | 2006038809 A * | 2/2006 |
| JP | U 3129670 | 3/2007 |
| WO | 2006-083776 | 8/2006 |
| WO | WO 2006/083776 | 8/2006 |

OTHER PUBLICATIONS

Chinese First Examination Report of China Application No. 200880014981.8, dated Jun. 9, 2011.

\* cited by examiner

First status    Second status (a)

(b)

(a) First status — Second status (b) First status — Second status (c)

SAMPLE INTRODUCTION DEVICE

BACKGROUND OF THE INVENTION

1. Field of the Invention

The present invention generally relates to a sample introduction device for guiding liquid samples into an analytical equipment, in particular, to a sample introduction device including a needle and an injection port connected to a flow path switching valve.

2. Description of Related Art

In order to analyze a plurality of samples, a sample introduction device for automatically guiding samples into an analytical equipment such as a liquid chromatograph in a specified sequence is adopted. FIG. 5(a) is a schematic view of a liquid chromatograph. The liquid chromatograph is formed of a liquid feeder 10, a sample introduction device 20, a separation/detection section 30, and a control/resolution section 40. The sample introduction device 20 is disposed between the liquid feeder 10 and the separation/detection section 30. The separation/detection section 30 includes an analysis column 31 and a detector 32, and various flow paths are formed for actual analysis purposes, thereby functioning as an analysis section. The liquid feeder 10, the sample introduction device 20, and the separation/detection section 30 are controlled by the control/resolution section 40. After receiving a signal from the detector 32, the control/resolution section 40 performs qualitative/quantitative resolution on the samples and saves the resolution data or files and outputs an analysis report.

The sample introduction device has the following two injection methods: a "total volume injection method" of injecting all measured samples from a sample container and a "partial injection method" of filling and injecting a part of the measured samples from the sample container into a sample loop (Patent Documents 1, 2, and Non-patent Document 1). In fields where only a few samples can be collected, the total volume injection method is widely applied for analysis for not wasting the collected samples.

FIG. 5(b) is a schematic view of flow paths inside the sample introduction device 20 for the total volume injection method. The sample introduction device 20 forms the flow paths centered with a six-port two-position valve 21 and a six-position valve 22. A flow path of a mobile phase solution from the liquid feeder 10 into the sample introduction device 20 is first connected to one port of the six-port two-position valve 21. A flow path, which is from the liquid feeder 10 and a flow path, which is toward the downstream side of separation/detection section 30 communicate with each other through a sample loop 23, a needle 24 disposed at a top section of the sample loop 23 and an injection port 25 inserted with the needle 24. Therefore, all samples filled in the needle 24 to the sample loop 23 are guided into the separation/detection section 30. The six-position valve 22 is connected to a flow path in communication with a cleaning fluid container, a flow path in communication with a metering pump 26 for drawing a cleaning fluid from the cleaning fluid container or drawing samples from a sample container 28, and a flow path in communication with a cleaning port 27 provided for the insertion of the needle 24 so as to clean the needle. Moreover, the needle 24 and the sample loop 23 are communicated with the flow path of the metering pump 26 through the six-port two-position valve 21. In addition, the six-port two-position valve 21 switches the flow path of the mobile phase solution pressurized by the liquid feeder 10 and is thus called a "high pressure valve". The six-position valve 22 is not connected to a flow path applied with a relatively high pressure and is thus called a "low pressure valve". Accordingly, in this specification, the six-port two-position valve may be referred to as the "high pressure valve" and the six-position valve may be referred to as the "low pressure valve".

To facilitate the understanding, a flow path switching valve, such as the high pressure valve 21 or the low pressure valve, 22 is illustrated. In the flow path switching valve, a stator surface disposed with holes is joined to a rotor surface disposed with grooves, and each groove on the rotor surface (rotor groove) communicates with two holes on the stator surface (stator holes). The rotor rotates to make the rotor surface slide relative to the stator surface, so that a relative position between the rotor groove and the stator holes is changed, thereby switching a communication status between one stator hole and the other stator holes. Moreover, the stator holes are in communication with the ports disposed on the flow path switching valve respectively and each port is connected to a flow path. Therefore, when the rotor rotates to cause a change of the relative position between the rotor groove and the stator holes, a communication status of the flow path connected to the port is switched.

FIGS. 8(a) to 8(c). 8 are diagrams respectively showing communication statuses of a joint surface of the high pressure valve 21 and the low pressure valve 22. The high pressure valve 21 in FIG. 8(a) is used for switching the flow paths into any of the two statuses. The high pressure valve 21 includes stator holes (a, b, c, d, e, and f) and arc-shaped rotor grooves (X, Y, and Z) centered with a rotation axis of the rotor. The high pressure valve 21 switches between a first status and a second status. In the first status, the rotor groove X communicates with the stator holes a and b, the rotor groove Y communicates with the stator holes c and d, and the rotor groove Z communicates with the stator holes e and f. In the second status, the rotor groove X communicates with the stator holes b and c, the rotor groove Y communicates with the stator holes d and e, and the rotor groove Z communicates with the stator holes f and a. In FIG. 5(b), in the high pressure valve 21, a port in communication with the stator hole a is connected to a flow path in communication with the needle 24 through the sample loop 23, a port in communication with the stator hole b is connected to a flow path in communication with the liquid feeder 10, a port in communication with the stator hole c is connected to a flow path in communication with the separation/detection section 30, and a port in communication with the stator hole d is connected to a flow path in communication with the injection port 25. The flow paths connected to a port in communication with the stator hole e and a port in communication with the stator hole f are determined according to the actual purposes and applications. When the high pressure valve 21 is in the first status, the flow path, which is from the upstream side of the liquid feeder 10 and the flow path, which is toward the downstream side of the separation/detection section 30 are communicated through the sample loop 23, the needle 24, and the injection port 25 (this status is also referred to as an "injection status"). When the high pressure valve 21 is in the second status, the flow path, which is from the upstream side of the liquid feeder 10 at and the flow path, which is toward the downstream side of the separation/detection section 30 are not communicated through the sample loop 23, the needle 24, and the injection port 25 (this status is also referred to as a "load status").

It takes tens of milliseconds to hundreds of milliseconds to switch between the first status and the second status. Generally, during this period, none of the stator holes are communicated, and in certain cases, a relatively long rotor groove is formed deliberately as mentioned in Non-patent Document 1. FIG. 8(b) depicts a high pressure valve in Non-patent Document 1, in which the rotor groove X is set longer than another rotor grooves Y and Z. The high pressure valve 21' performs the following functions, which are using a metering pump to repeatedly draw and discharge samples and filling the samples into a sample loop having a volume greater than or equal to that of the metering pump while remaining in the load status. The high pressure valve 21' is obtained through improvement on the structure disclosed in Patent Document 2.

The low pressure valve 22 in FIG. 8(c) is used for switching between six communication statuses, so as to enable a common port to be communicated with the other ports and/or enable various ports to be communicated with each other. The low pressure valve 22 includes stator holes (h, p, r, s, t, and u) and rotor grooves (V and W). The stator hole h is always connected to one end of the rotor groove V and is also in communication with the common port of the low pressure valve 22. The metering pump 26 or the cleaning port 27 and the cleaning fluid container are connected to the other ports of the low pressure valve 22 and are also connected to the ports of the high pressure valve 21, so as to be in communication with the needle 24 and the injection port 25. In FIG. 5(b), the common port in communication with the stator hole h is connected to the flow path connected with the metering pump 26. Samples are drawn or discharged from the sample container 28 and the cleaning fluid is drawn or discharged through the switching of the low pressure valve 22. Further, in order to accurately draw with the metering pump 26, the pressure in a sampling flow path (through the needle 24 and the sample loop 23) is at the atmospheric pressure, or other measures are taken. In addition, a low pressure valve without a common port is used in Non-patent Document 1.

Patent Document 1: Japanese Patent Publication No. H06-148157
Patent Document 2: Japanese Patent Publication No. H10-170488
Non-patent Document 1: "HPLC//LCtalk No. 46 TEC, INJECTION METHODS OF SAMPLE INTRODUCTION DEVICE (COMPARISON BETWEEN TOTAL VOLUME INJECTION METHOD AND PARTIAL INJECTION METHOD)", Shimadzu Corporation, online, http://www.an.shimadzu.co.jp/support/lib/lctalk/46/46tec.htm, searched on Sep. 25, 2007.

In the total volume injection method shown in FIG. 5(b), when the high pressure valve 21 is in the load status, a specified volume of samples are drawn from the sample container 28 through the needle 24 and then filled into the sample loop 23 connected to a bottom section of the needle 24. Thereafter, the needle 24 is moved to the cleaning port 27 to have its outer surface cleaned. Afterward, the needle 24 is inserted into the injection port 25, and the high pressure valve 21 is switched to the injection status. The circulation of the mobile phase solution inside the sample loop 23 forces the samples filled in the sample loop 23 out and guides all the samples into the separation/detection section 30. For the guided samples, the high pressure valve remains in the injection status till the analysis is over. That is, during the analysis, the mobile phase solution keeps flowing inside the needle 24. In other words, the mobile phase solution remains in a cleaning status inside the needle 24.

Although the outer side of the needle 24 is cleaned at the cleaning port 27 and the inner side thereof is cleaned with the mobile phase solution, the problem of carry-over may still occur. The so-called carry-over means a phenomenon that a part of the injected samples are left behind and affect the next round of analysis. Although the carry-over is greatly alleviated through the surface treatment of the needle, the cleaning of the needle, and the change of the shape of the injection port, the problem still remains. Meanwhile, with the development of ultra-micro analysis and highly sensitive detection in recent years, the problem is growing worse. Therefore, the carry-over impedes the accurate analysis on the volume of samples drawn from the sample container 28.

After careful researches, the inventor of the present invention has identified the reason why carry-over still occurs even if the needle 24 is cleaned in the process of switching the high pressure valve from the load status to the injection status.

The switching of the flow paths is realized through the operation of the high pressure valve 21 and the processes for forming of the status, in which the rotor grooves respectively communicate with the stator holes, are greatly related through the operation. As shown in FIG. 8(a), even if the three rotor grooves have the same length, the rotor surface and the stator surface sliding repeatedly may still be abraded due to long-time use; thus, the sections for forming the rotor grooves or the stator holes may be damaged. According to the different damaged sections, a status having the same effect as that formed with a relatively longer rotor groove is obtained. As a result, flow paths communicated in a time sequence different from the original one are generated. According to different damaged sections and degrees of the damage, the high pressure valve 21 becomes a valve as shown in FIG. 8(b). As described above, the high pressure valve in FIG. 8(b) is applicable for processing samples having a large volume (from hundreds of μl to several ml) exceeding a 1-stroke volume of the metering pump 26, but is not suitable for processing a minute volume of the samples.

FIGS. 6(a) to 6(d) show the flowing directions of the samples at a circumference of an insertion section of the needle 24 and the injection port 25, as well as the samples inside the needle 24 in a period from the moment that the high pressure valve 21' is switched to the injection status immediately after the needle 24 is inserted into the injection port 25 till the moment that all the samples flow to the downstream side. FIGS. 6(a) to 6(d) also show a generation mechanism of carry-over caused by the abraded high pressure valve 21'.

First of all, FIG. 6(a) shows a status that the needle 24 is inserted into the injection port 25 after the sample solution is measured. Till the high pressure valve 21' is switched from the load status to the injection status, the samples are located at a tip section inside the needle 24 and the needle 24 is filled with the mobile phase solution in a manner of holding the samples.

Referring to FIG. 6(b), during the switching from the load status to the injection status, only the rotor groove X communicates with the stator holes a and b among the three rotor grooves, enabling the liquid feeder 10 and the needle 24 to communicate with each other. At this time, a part of the samples are forced out of the tip section of the needle 24 into the injection port 25 under the pressure of the liquid feeder 10. In this case, as the injection port 25 does not communicate with the separation/detection section 30, and the samples cannot flow to the downstream side, so that the part of the samples under the pressure of the liquid feeder are forced into a gap between the tip section of the needle 24 and the injection port 25 (FIG. 6(c)). The section marked by a circle in FIG. 6(c) is an amplified view of the tip section of the needle. A gap exists between the tip section of the needle 24 after taper machining and an inner wall of the injection port 25 substantially formed perpendicularly thereto, so that the samples are forced into the gap.

Afterward, the injection port 25 is in communication with the separation/detection section 30, and the samples are guided into the separation/detection section 30 under the influence of the mobile phase solution delivered by the liquid feeder 10. However, the portions of the samples that are forced into the gap are not guided into the separation/detection section 30, but are left in the injection port 25 instead (FIG. 6(d)). That is, as for the carry-over that still occurs even if the needle 24 is cleaned, during the switching from the load status to the injection status, the communication between the needle 24 and the liquid feeder 10 (the stator holes a and b communicate with each other through the rotor groove X) results in carry-over more easily, when compared with the communication between the injection port 25 and the separation/detection section 30 (the stator holes c and d communicates with each other through the rotor groove Y).

SUMMARY OF THE INVENTION

The present invention is directed to reducing the carry-over by decreasing a volume of samples forced into a gap in an insertion section of a needle and an injection port.

In order to achieve the above object, the present invention provides a sample introduction device, which includes a flow path switching mechanism. The flow path switching mechanism includes a stator, a rotor, and a flow path switching valve. The stator is configured with six holes at a circumference on a surface of the stator. The rotor is slidably joined with the stator surface and includes three grooves for communicating two adjacent holes at the circumference on the stator surface. The flow path switching valve includes six ports in communication respectively with the six holes, so that the rotor rotates to switch between combinations of the holes that are in communication with the grooves. The six ports are at least connected to a) a flow path in communication with a sample loop provided with a needle on a top section, b) a flow path in communication with a liquid feeder for delivering a solution, c) a flow path in communication with an analysis section for analyzing samples, and d) a flow path in communication with an injection port inserted with the needle. The flow path switching valve switches between a first status of which the liquid feeder is in communication with the analysis section through the sample loop and the injection port, and a second status of which the liquid feeder is in communication with the analysis section not through the sample loop and the injection port. For the sample introduction device, the rotor groove for communicating the injection port and the analysis section in the first status is cut longer than the rotor groove for communicating the liquid feeder and the sample loop in the first status.

Furthermore, for the sample introduction device, the rotor groove for communicating the injection port and the analysis section in the first status is cut relatively longer in a rotation direction when switching from the first status to the second status.

According to the above structure, when the high pressure valve is switched from the second status to the first status, the communication between the injection port and a port connected to a flow path toward a separation/detection section occurs earlier than the communication between a port connected to a flow path in communication with the liquid feeder and a port connected to a flow path in communication with the needle through the sample loop. During the switching of the flow path switching valve, by communicating the injection port and the port connected to the flow path toward the separation/detection section as early as possible, a pressure difference is generated between a pressure (residual pressure) of the analysis section and a pressure of a sampling section at the atmospheric pressure, so as to force the samples at the tip section of the needle into the needle. In addition, a mobile phase solution may also exist at the tip section of the needle to replace the samples.

EFFECT OF THE INVENTION

In the sample introduction device in a total volume injection method, when the flow paths are switched to guide a sample into the separation/detection section at the downstream side, the sample remained between the tip section of the sample needle and the injection port is decreased, thereby mitigating the chances that the residual sample and a next sample are guided together; that is, the problem of carry-over is alleviated. Moreover, accurate quantification may be performed on the samples and the precision of the analysis is improved due to the alleviation of the carry-over. In ultra-micro analysis that is greatly affected by the carry-over, the precision of the analysis is significantly improved. Since the present invention is realized by changing a length of the rotor groove in a joint section between the stator surface and the rotor surface, other tubing sections or controls may be configured the same as the device in the prior art.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

Figure 1:
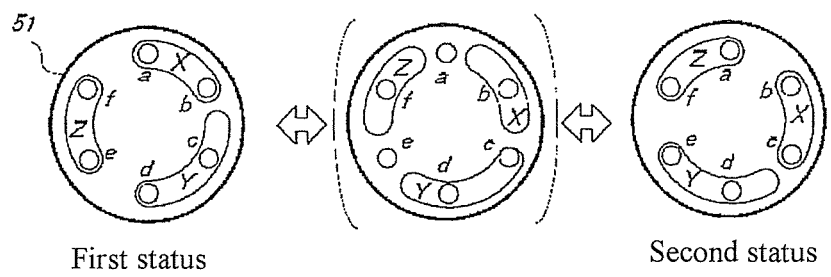
FIGS. 1(a) to 1(b) are diagrams illustrating a high pressure valve (six-port two-position valve) of a sample introduction device according to the present invention.
Figure 1:
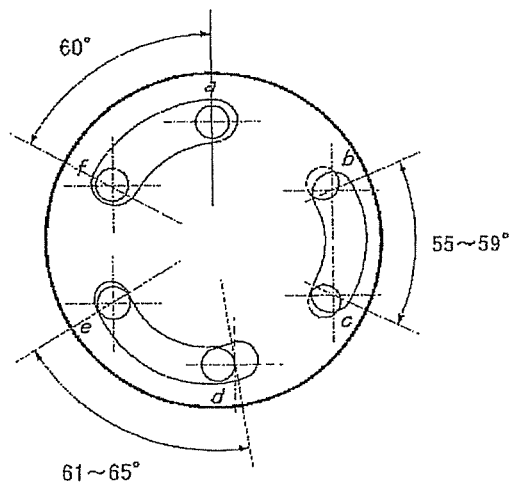

LIST OF SYMBOLS 10 liquid feeder
20, 50 sample introduction device
21, 51 6-port 2-position valve (high pressure valves)

22, 52 6-position valve (low pressure valve)
23, 53 sample loop
24, 54 needle
25, 55 injection port
26, 56 metering pump
27, 57 cleaning port
28, 58 sample container
29 intermediate liquid
30 separation/detection section
31 column
32 detector
40 control/resolution section

DESCRIPTION OF THE EMBODIMENTS

Reference will now be made in detail to the present embodiments of the invention, examples of which are illustrated in the accompanying drawings. Wherever possible, the same reference numbers are used in the drawings and the description to refer to the same or like parts.

A sample introduction device of the present invention is illustrated below with the accompanying drawings.

A high pressure valve of the sample introduction device according to the present invention has the following characteristics. Referring to FIG. 1, the high pressure valve 51 includes a stator and a rotor. The stator is configured with six stator holes a to f arranged at a circumference with an equal interval. The rotor is provided with a rotor groove X for switching the stator hole b to the stator hole a or c for communication, a rotor groove Y for switching the stator hole d to the stator hole c or e for communication, and a rotor groove Z for switching the stator hole f to the stator hole a or e for communication. The rotor groove Y is longer than a length for merely communicating with the stator holes c and d or merely communicating with the stator holes d and e, and is also longer than the rotor groove X. For the purpose of illustration, when "the length of the rotor groove for communicating two adjacent stator holes among the six stator holes arranged at the circumference with an equal interval" is referred to as a "60° arc"; the rotor grooves X and Z are 60° arcs and the rotor groove Y is a 61° to 65° arc. Therefore, when the rotor groove Y is in a load status (a second status that the stator holes d and e are in communication with each other), a residual section is present at a side of the stator hole d that is in communication with the injection port. When the rotor groove Y is in an injection status (a first status that the stator holes c and d are in communication with each other), a residual section is present at a side of the stator hole c in communication with a port connected to a flow path toward the separation/detection section 30.

If the rotor groove Y is longer than the rotor groove X, the rotor groove X or the rotor groove Z may be configured to be shorter than the usual circumstance (a 60° arc). For example, if the rotor groove Y is a 60° arc, the rotor grooves X and Z are 55° to 59° arcs. That is, in the injection status, the rotor groove Y may be set at a length for merely communicating the stator holes c and d, the rotor groove X may be set at a length that two ends of the rotor groove X do not completely cover the stator holes a and b, and the rotor groove Z may be set at a length that two ends of the rotor groove Z do not completely cover the stator holes e and f.

The lengths of the rotor grooves are illustrated in FIG. 1(b). Referring to FIG. 1(b), a groove communicating with the stator holes a and f is at an angle of 60°, a groove communicating with the stator holes b and c is at an angle of 55° to 59°, and a groove communicating with the stator holes d and e is at an angle of 61° to 65°. These angles are respectively formed between the intersection points of the center lines of two adjacent stator holes and a center of the rotor. As for the length of the rotor groove, when it is assumed that the two stator holes are in a position relation determined by the angles, the length of the groove is just a length for communicating the two stator holes. In this specification, the rotor groove is depicted to be relatively longer. In a high pressure valve of a liquid chromatograph for processing minute flow rates of several μL to several mL/min, a diameter of a joint section between the rotor surface and the stator surface is about 5 mm. A width of the rotor groove is hundreds of μm and a length thereof is several mm. A diameter of the stator hole is hundreds of μm.

Referring to FIGS. 2(a) to 2(d), the sample introduction device 50 includes a high pressure valve 51. The sample introduction device 50 forms a flow path centered with the high pressure valve 51 and a low pressure valve 52. A flow path of a mobile phase solution from the liquid feeder 10 into the sample introduction device 50 is first connected to one port of the high pressure valve 51. As a flow path, which is from the upstream side of the liquid feeder 10 and a flow path, which is toward the downstream side of the separation/detection section 30 communicate with each other through the sample loop 53, a needle 54 disposed at a top section of the sample loop 53 and an injection port 55 inserted with the needle 54. Therefore, all samples filled in the needle 54 to the sample loop 53 are guided into the separation/detection section 30. The low pressure valve 52 is connected to a flow path in communication with a cleaning fluid container, a flow path in communication with a metering pump 56 for drawing a cleaning fluid from the cleaning fluid container or drawing samples from a sample container 58, and a flow path in communication with a cleaning port 57 for insertion of the needle 54 so as to clean the needle. Moreover, the needle 54 and the sample loop 53 are communicated with the flow path of the metering pump 56 through the high pressure valve 51. In addition, referring to FIGS. 2(a) to 2(d) and 5(b), other elements constituting the sample introduction device, besides the high pressure valve 51, may be the same.

Figure 2:
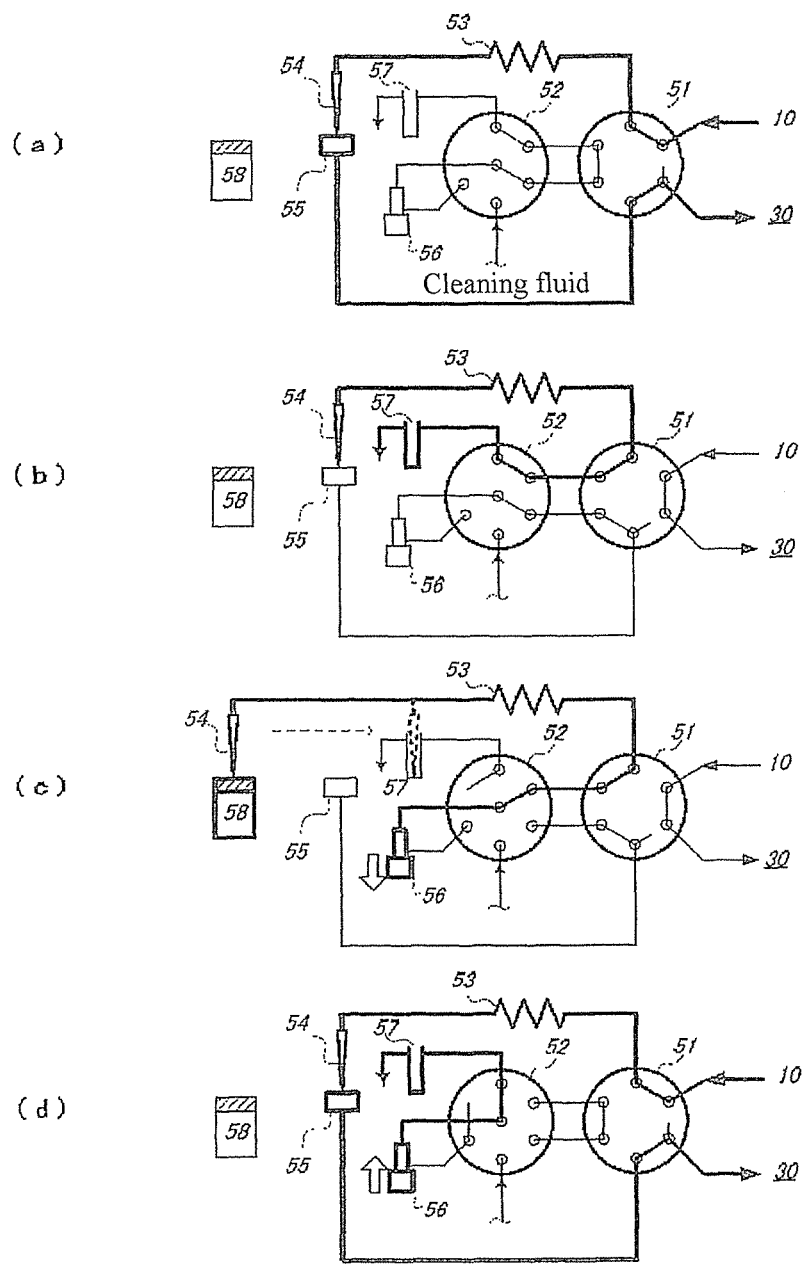
FIG. 2(a) shows a flow path in a standby status.
FIG. 2(b) shows a flow path when a pressure of a sampling flow path is open.
FIG. 2(c) shows a flow path when samples are drawn and a needle is cleaned.
FIG. 2(d) shows a flow path when the samples are guided.

In a period of drawing samples from the sample container 58 (in a standby status before new samples are guided), the communication status inside the sample introduction device 50 is shown in FIG. 2(a), and the high pressure valve 51 is in an injection status. As the liquid feeder 10 delivers the mobile phase solution with a high pressure (several MPa to tens of MPa), a pressure of the sampling flow path needs to be at the atmospheric pressure before the samples are drawn. That is, as shown in FIG. 2(b), the high pressure valve 21 turns into a load status. In another aspect, the low pressure valve 52 is in a status that the needle 54, the sample loop 53, and the cleaning port 57 are in communication, and the injection port 55 and the metering pump 56 are in communication. Therefore, the sampling flow path is open to the atmospheric pressure.

Then, referring to FIG. 2(c), the low pressure valve 52 rotates to enable the needle 54 to communicate with the metering pump 56 through the sample loop 53, the high pressure valve 51, and the low pressure valve 52. Moreover, a moving mechanism (not shown) is employed to allow the needle 54 to depart from the injection port 55 and to immerse in the samples inside the sample container 58. Thereafter, the metering pump 56 operates to draw a required volume of the samples from the sample container 28. After the required volume of the samples is drawn, referring to the dotted line in FIG. 2(c), the needle 54 is inserted into the cleaning port 57 to have its outer side cleaned by the cleaning fluid stored in the cleaning port 57.

Figure 3:
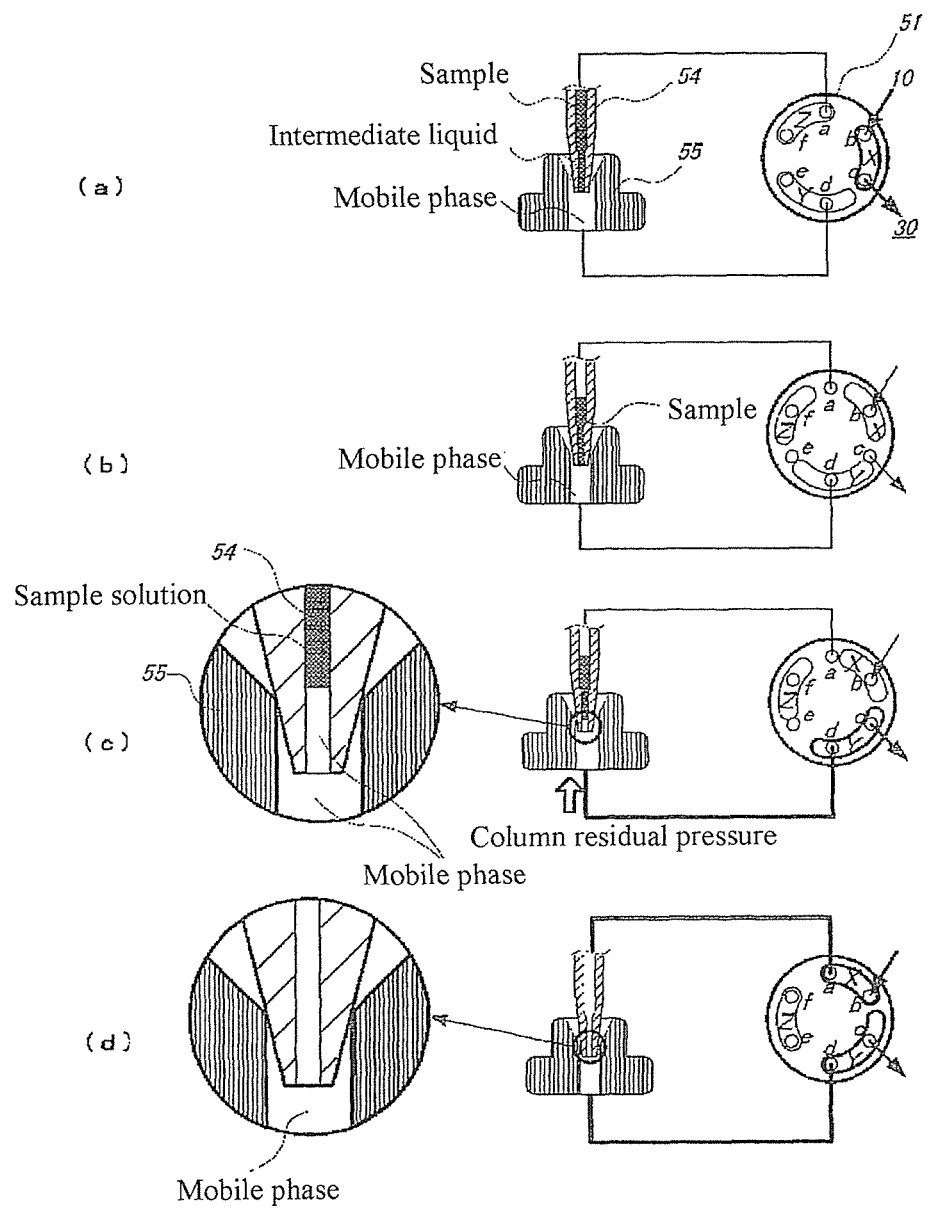
FIGS. 3(a) to 3(d) are diagrams showing statuses of samples at an insertion section of a sampling and injection port in the sample introduction device according to the present invention.

FIGS. 3(a) to 3(d) show the flowing directions of the liquid inside the needle 54 in a period from the moment that the needle 54 is inserted into the injection port 55 till the moment that the high pressure valve 51 is switched from the load status to the injection status. As shown in FIG. 3(a), after the needle 54 is inserted into the injection port 55, the samples remain at a tip section of the needle 54.

When the high pressure valve 51 is switched from the load status to the injection status, the positions of the rotor grooves X, Y, and Z change with the rotation of the rotor; thus, as shown in FIG. 3(b), the stator holes b, d, and f are in a status of being not in communication with the adjacent stator holes.

When the rotor further rotates to change the positions of the rotor grooves X, Y, and Z, as shown in FIG. 3(c), only the rotor groove Y is in a status of communicating with the two stator holes c and d. The stator hole c is in communication with the separation/detection section 30 at the downstream side. The stator hole d is in communication with the injection port 55. Before the high pressure valve 51 is switched from the load status to the injection status, in the load status, a liquid is input from the liquid feeder 10 to the separation/detection section 30 and the pressure is kept rising due to liquid delivery. In another aspect, after the sampling flow path or the injection port 55 is open to the atmospheric pressure, the needle 54 draws in the samples and is inserted into the injection port 55. A pressure at the insertion section is approximately the atmospheric pressure. When only the rotor groove Y communicates with the two stator holes c and d, a pressure is released from the separation/detection section 30 at a high pressure side to the needle 54 at a low pressure side. At this time, the liquid at the tip section of the needle 54 is forced into the side of the high pressure valve 51. However, the stator hole a of the high pressure valve 51 in communication with the needle 54 at this time is not communicated to any section; the stator hole a of the high pressure valve 51 is thus sealed, so that quite a small volume of the liquid is forced into the valve.

Subsequently, as shown in FIG. 3(d), the needle 54 is in communication with the liquid feeder 10 through the sample loop 53 and the high pressure valve 51 (operating with the stator holes a, b and the rotor groove X). After the sample solution is pressurized by the mobile phase solution from the liquid feeder 10, the samples that are already filled in the sample loop 53 are guided from the needle 54 into the separation/detection section 30 at the downstream side through the injection port 55. The guided samples are analyzed in the injection status and the mobile phase solution keeps flowing to the insertion section of the needle 24 and the injection port 55, so that the samples may not remain in the gap.

During the analysis, as shown in FIG. 2(d), the low pressure valve 52 rotates to enable the metering pump 56 to communicate with the cleaning port 57. The metering pump 56 operates to discharge the cleaning fluid in the flow path of the plunger pump 52 to the cleaning port 57, and to further discharge the cleaning fluid to a drain.

The configuration and functions of the sample introduction device of the present invention for reducing carry-over are described above. Moreover, an actual measurement example showing the effect of reducing the carry-over by using the sample introduction device of the present invention is given below. In order to show a carry-over volume herein, a caffeine aqueous solution is adopted as a sample for analysis and an area α of a peak of a chromatogram is obtained for the caffeine aqueous solution. Then, the same analysis is conducted on a liquid having the same composition as the mobile phase solution (a blank sample), so as to calculate an area β of a peak within the same holding time as the caffeine aqueous solution. Afterward, a ratio of β to α is determined to be a carry-over volume. The actual measurement is employed for the sample introduction device in the prior art and the sample introduction device of the present invention.

[Analysis Conditions]

| | |
|---|---|
| Sample | 250 mg/L Caffeine Aqueous Solution |
| Sample Injection Volume | 10 μL |
| Mobile Phase Composition | Water:Methanol = 4:1 |
| Flow Rate | 0.8 mL/min (Liquid Delivery Pressure: 64 MPa) |
| Column | Reverse-phase Column (Inner Diameter 2 mm × Length 100 mm) |
| Detector | UV-visible Spectro-photometric Detector (Detection Wavelength: 272 nm) |

Figure 4:
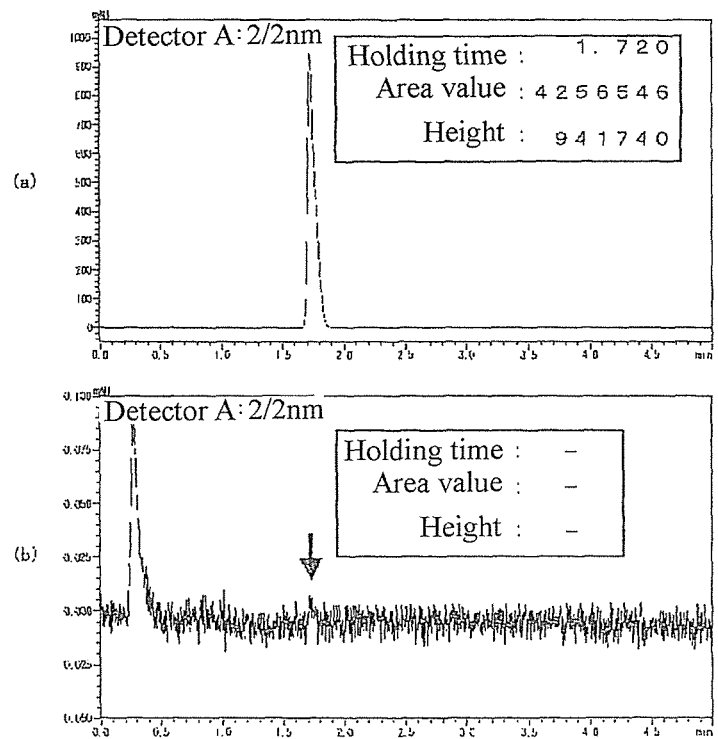
FIGS. 4(a) to 4(b) are chromatograms of a carry-over test obtained through the sample introduction device of the present invention.
Figure 5:
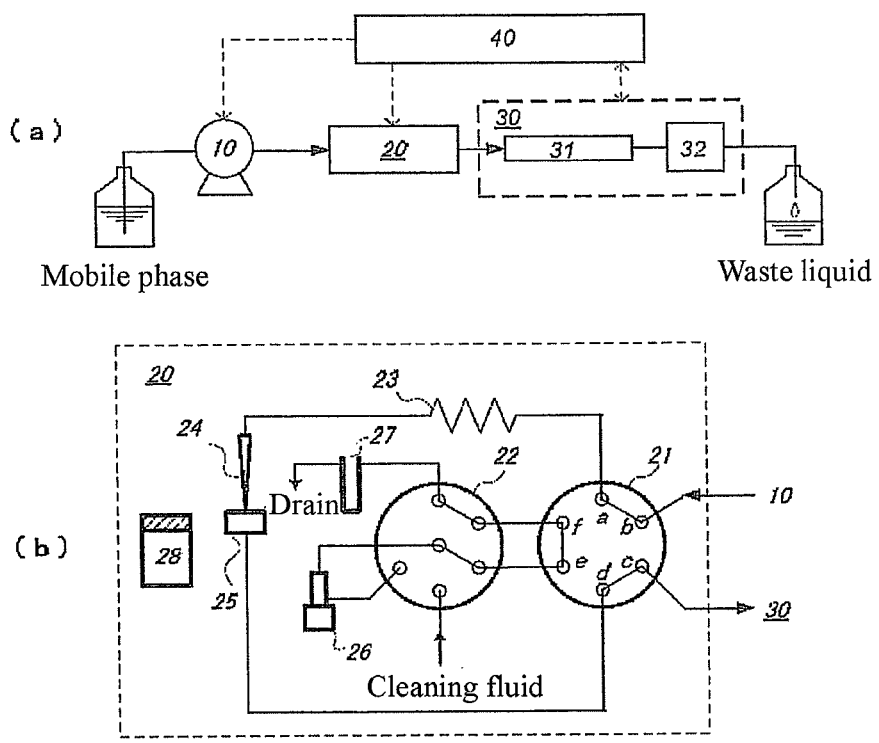
FIG. 5(a) is a schematic view of a structure of a liquid chromatograph.
FIG. 5(b) is a schematic view of a flow path of the sample introduction device in a total volume injection method.
Figure 6:
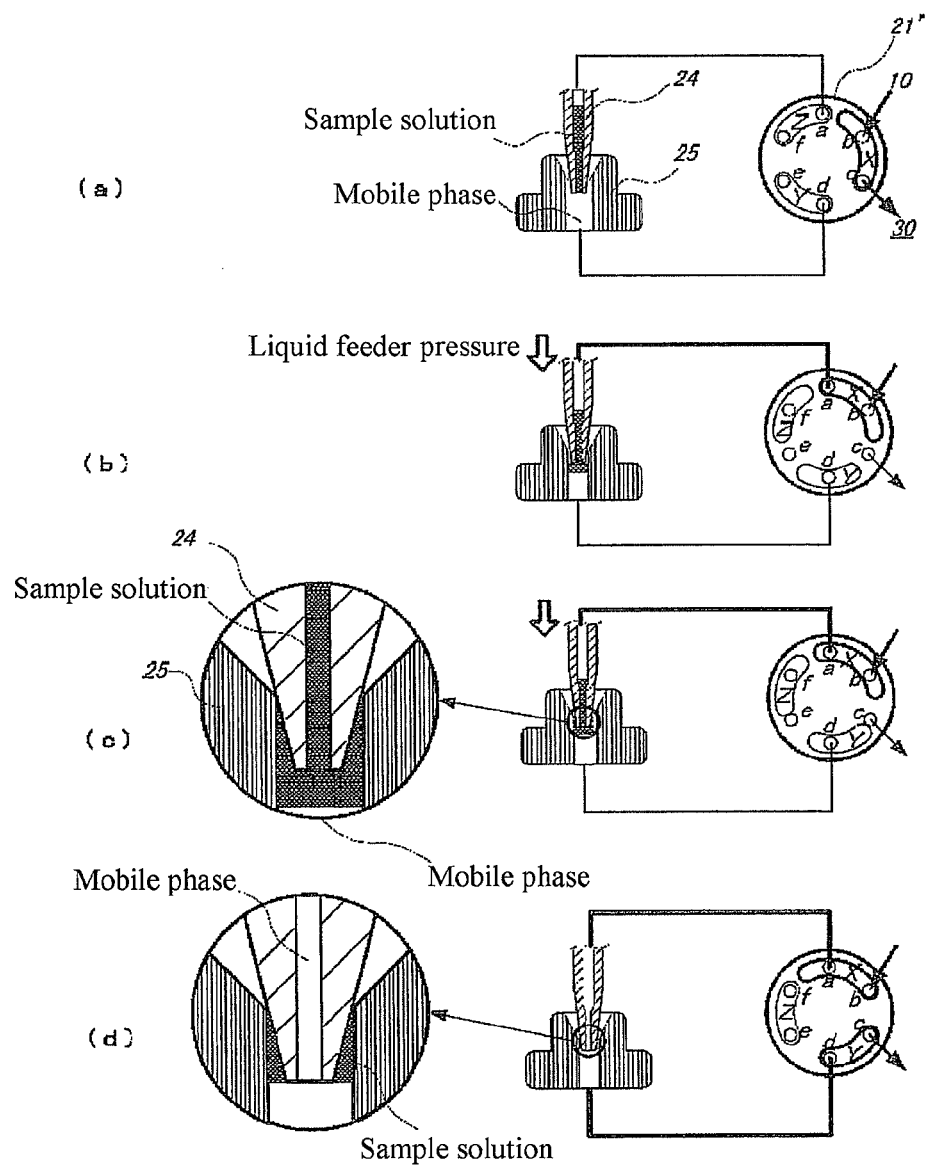
FIGS. 6(a) to 6(d) are diagrams showing statuses of samples at an insertion section of a sampling and injection port in a sample introduction device in the prior art.

FIGS. 7(a) and 7(b) show chromatograms obtained through the sample introduction device in the prior art. FIG. 7(a) is a chromatogram of the caffeine aqueous solution, and FIG. 7(b) is a chromatogram of the blank sample. FIGS. 4(a) and 4(b) are s chromatograms obtained through the sample introduction device of the present invention. FIG. 4(a) is a chromatogram of the caffeine aqueous solution, and FIG. 4(b) is a chromatogram of the blank sample. The scales on the time axes of all the chromatograms, that is, the horizontal axes, are the same. However, as for the scales on the intensity axes, that is, the longitudinal axes, the scales in FIGS. 7(b) and 4(b) are much smaller than those in FIGS. 7(a) and 4(a).

Figure 7:
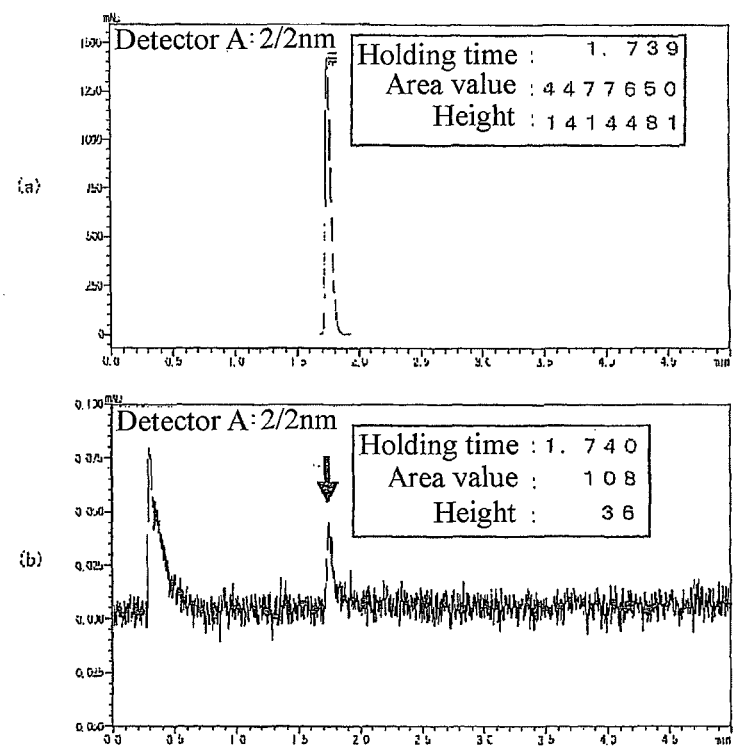
FIGS. 7(a) to 7(b) are chromatograms of a carry-over test obtained through the sample introduction device in the prior art.
Figure 8:
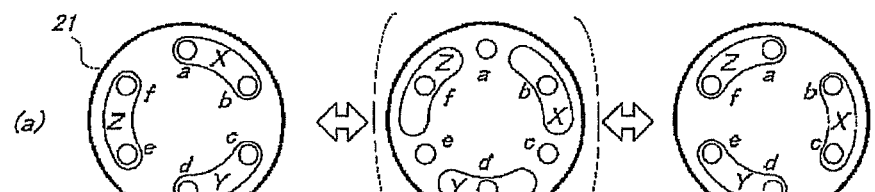
FIGS. 8(a) to 8(c) are diagrams illustrating switched statuses of a high pressure valve (a six-port two-position valve) and a low pressure valve (a six-position valve).
Figure 8:
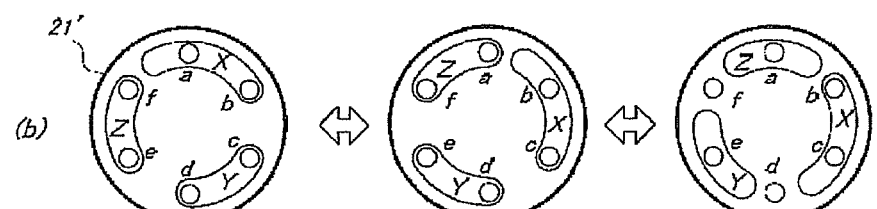
Figure 8:
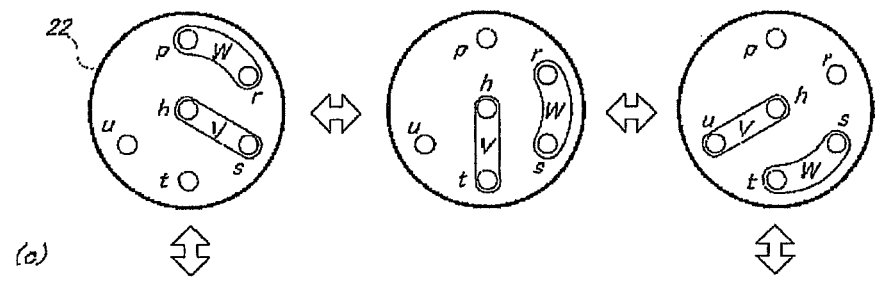
Figure 8:
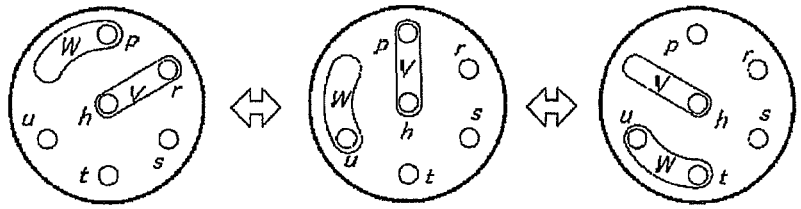

It can be seen from FIG. 7 that, for the sample introduction device in the prior art, an area α of a peak corresponding to the detected caffeine in the analysis of the caffeine aqueous solution is 4477650, an area β of a peak corresponding to the detected caffeine in the analysis of the blank sample is 108, and a carry-over volume β/α is 0.002%.

It can be seen from FIGS. 4(a) and 4(b) that, for the sample introduction device of the present invention, an area α of a peak corresponding to the detected caffeine in the analysis of the caffeine aqueous solution is 4256546, an area β of a peak corresponding to the detected caffeine in the analysis of the blank sample is 0 (undetectable), and a carry-over volume β/α is 0.000%. That is to say, the carry-over may not occur in the sample introduction device of the present invention.

In view of the above, the carry-over is greatly reduced with the sample introduction device of the present invention. In addition, the sample introduction device in the prior art for comparison with the present invention is the same as that disclosed in Registered Utility Model Patent No. 3129670 obtained by improving the device described in Japanese Patent Publication No. 2006-38809. For the purpose of illustration, the flow path between the injection port 25 and the high pressure valve 21 is extended to avoid intersections of the flow paths in the figures. However, in order to shorten the analysis time or reduce the dead volumes, the flow path is preferably short. Alternatively, referring to the device disclosed in Japanese Patent Publication No. 2004-215118, the injection port 25 is directly disposed on the port of the high pressure valve 21. Moreover, it is clearly depicted in the figures that the sample loop 23 has a spiral section. Definitely, the sample loop 23 may also not have a spiral section, like the device disclosed in Japanese Patent Publication No. 2004-85499, as long as a required volume of the sample loop 23 is ensured. The characteristics of the sample introduction devices disclosed in the aforementioned documents are all applicable to the sample introduction device of the present invention.

Figure 9A:
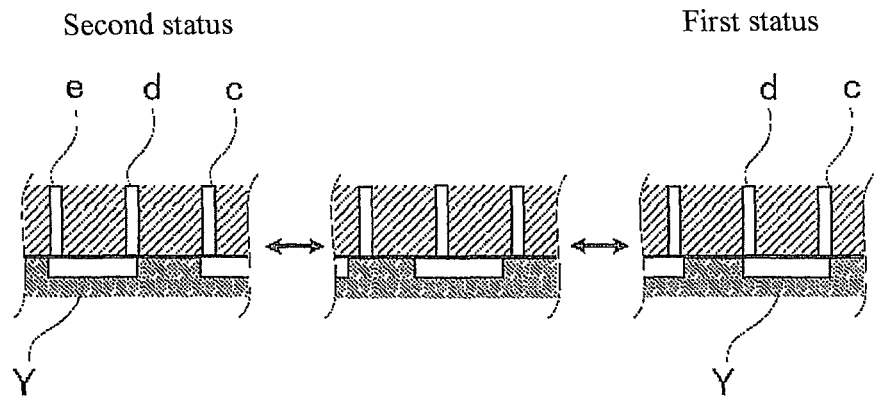
FIGS. 9(a) to 9(c) are sectional views of position relations between holes and grooves near a joint surface between a rotor and a stator of the high pressure valve.
Figure 9B:
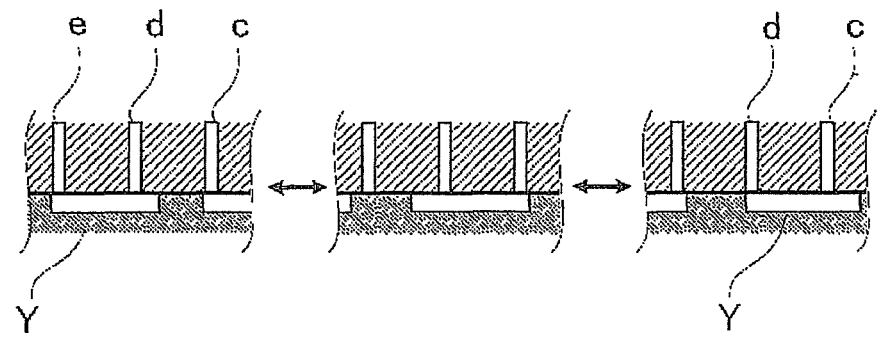
Figure 9C:
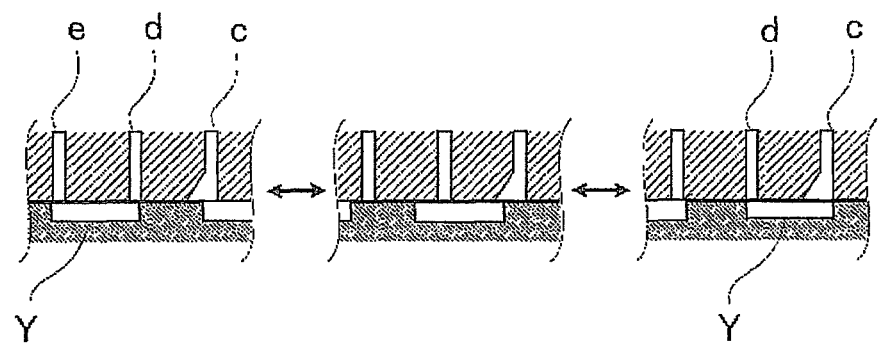

Alternatively, in addition to extending the length of the groove cut on the rotor in a specific direction, an aperture of a hole that penetrates the stator surface (the joint surface between the stator and the rotor) is enlarged and a center of the hole is deviated from the center of the stator hole to achieve the same effect. FIGS. 9(a) and 9(c) are sectional views near the joint surface including the stator holes (e, d, and c) and the rotor groove Y, and FIGS. 9(a) and 9(c) show the switching from a status that the stator holes e and d are in communication (the second status) to a status that the stator holes d and c are in communication (the first status). FIG. 9(a) shows the prior art, FIG. 9(b) shows the extension of the length of the rotor groove, and FIG. 9(c) shows the enlargement of the stator holes. According to the above description, during the switching from the second status to the first status, the rotor groove Y in the prior art in FIG. 9 (a) does not communicate with the two stator holes and is cut relatively longer. In FIG. 9(b), in the middle of the switching, the two stator holes start to communicate, and the valve is switched to the first status. In FIG. 9(c), instead of extending the length of the groove, an aperture of the stator hole c is merely enlarged by tens of μm on the stator surface and is deviated toward the side of the stator hole d. In this case, similar to FIG. 9 (b), the two stator holes start to communicate in the middle of the switching, and the valve is switched to the first status to achieve the same purpose as mentioned above.

The above descriptions are merely an embodiment of the present invention, and modifications and variations can be made without departing from the scope of the invention. It should be understood that these modifications and variations also fall within the protection scope of the present invention.

What is claimed is:

1. A sample introduction device, comprising a flow path switching mechanism, wherein the flow path switching mechanism comprises a flow path switching valve that comprises:
   a stator, comprising six holes at a circumference on a stator surface;
   a rotor, slidably joined with the stator surface, and comprising three grooves each for communicating with two adjacent holes at the circumference on the stator surface; and
   six ports in communication respectively with the six holes, so that the rotor rotates to switch between combinations of the holes that are in communication with the grooves, wherein
   the six ports are at least connected to a) a flow path in communication with a sample loop provided with a needle on a top section of the sample loop, b) a flow path in communication with a liquid feeder for delivering a solution, c) a flow path in communication with an analysis section for analyzing a sample, and d) a flow path in communication with an injection port inserted with the needle,
   the flow path switching valve switches between a first status that the liquid feeder is in communication with the analysis section through the sample loop and the injection port, and a second status that the liquid feeder is in communication with the analysis section not through the sample loop and the injection port, and
   the rotor groove communicating the injection port and the analysis section in the first status is longer than the rotor groove communicating with the liquid feeder and the sample loop in the first status, is extended, in the first status, at a side of the flow path a in communication with the sample loop, and communicates, in the second status, the flow path b in communication with the liquid feeder and the flow path c in communication with the analysis section, so that the sample at a tip section of the needle is forced into the needle at beginning of switching from the second status to the first status.

2. The sample introduction device according to claim 1, wherein the rotor groove communicating with the injection port and the analysis section in the first status is extended, in a rotation direction of switching from the first status to the second status, so that it biases toward the rotor groove communicating with the liquid feeder and the sample loop in the first status.

3. A sample introduction device, comprising a flow path switching mechanism, wherein the flow path switching mechanism comprises a flow path switching valve that comprises:
   a stator, comprising six holes configured at a circumference on a stator surface;
   a rotor, slidably joined with the stator surface, and comprising three grooves each for communicating with two adjacent holes at the circumference on the stator surface; and
   six ports in communication respectively with the six holes, so that the rotor rotates to switch between combinations of the holes that are in communication with the grooves, wherein
   the six ports are at least connected to a) a flow path in communication with a sample loop provided with a needle on a top section of the sample loop, b) a flow path in communication with a liquid feeder for delivering a solution, c) a flow path in communication with an analysis section for analyzing a sample, and d) a flow path in communication with an injection port inserted with the needle,
   the flow path switching valve switches between a first status, in which the liquid feeder is in communication with the analysis section through the sample loop and the injection port, and a second status, in which the liquid feeder is in communication with the analysis section not through the sample loop and the injection port, and
   the stator hole in communication with the port connected to a flow path toward the analysis section is opened on a joint surface of the rotor is enlarged toward a side of the stator hole in communication with the port connected to a flow path toward the injection port, so that the sample at a tip section of the needle is forced into the needle at beginning of switching from the second status to the first status.

* * * * *